(12) United States Patent
Furukawa et al.

(10) Patent No.: US 8,794,760 B2
(45) Date of Patent: Aug. 5, 2014

(54) IMAGE PROCESSING APPARATUS AND METHOD

(75) Inventors: Daisuke Furukawa, Koganei (JP); Yuta Nakano, Kawasaki (JP); Kenji Morita, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 489 days.

(21) Appl. No.: 13/051,391

(22) Filed: Mar. 18, 2011

(65) Prior Publication Data

US 2011/0242484 A1 Oct. 6, 2011

(30) Foreign Application Priority Data

Apr. 5, 2010 (JP) ................................. 2010-087348

(51) Int. Cl.
*A61B 3/14* (2006.01)
*A61B 3/00* (2006.01)

(52) U.S. Cl.
CPC ........................................ *A61B 3/14* (2013.01)
USPC ........................................... 351/206; 351/246

(58) Field of Classification Search
USPC .................................................. 351/206, 246
See application file for complete search history.

(56) References Cited

U.S. PATENT DOCUMENTS 6,293,674 B1 9/2001 Huang et al.

*Primary Examiner* — Jack Dinh
(74) *Attorney, Agent, or Firm* — Fitzpatrick, Cella, Harper & Scinto

(57) ABSTRACT

An image processing apparatus for supporting imaging diagnosis of an eye is provided. A layer boundary of a retina region is detected from a tomographic image. A position where the detected layer boundary intersects with an upper or lower limit position of the image in the depth direction of the tomographic image is determined as a dividing position. The tomographic image is divided at the determined dividing position by a scan line in the depth direction of the tomographic image. Subsequently, whether the detection is a false detection is judged for each divided region. An average density value of the image outside the retina region according to the detected result is calculated for each divided region, and the detection in the divided region is judged to be a false detection if the average density value is equal to or greater than a predetermined threshold.

19 Claims, 7 Drawing Sheets

IMAGE PROCESSING APPARATUS AND METHOD

BACKGROUND OF THE INVENTION

1. Field of the Invention

The present invention relates to an image processing apparatus and a method for supporting imaging diagnosis of an eye, and particularly, to an image processing apparatus and a method using a tomographic image of an eye.

2. Description of the Related Art

In recent years, eyes are often inspected to provide early diagnosis of diseases that are ranked high in causing lifestyle-related diseases and blindness. Tomographic eye image pickup apparatus, such as those for Optical Coherence Tomography (OCT), can observe in three-dimensions, the state inside a retinal layer, and the apparatus are expected to be useful in providing a more accurate diagnosis of a disease.

FIG. 3 shows a schematic diagram of a topographic image of a macular area of a retina taken by OCT. OCT takes an image of an eye to acquire a volume image formed by a set of a plurality of two-dimensional tomographic images. In FIG. 3, $T_1$ to $T_n$ denote two-dimensional tomographic images (B scan images, hereinafter called "tomographic images"). In each tomographic image $T_k$, the horizontal direction of the tomographic image is defined as an X-axis direction, and the depth direction is defined as a Z-axis direction. The lines parallel to the Z axis of the tomographic image will be called A scan lines. In the tomographic image $T_k$, $L_1$ denotes an inner limiting membrane, $L_2$ denotes a boundary of a nerve fiber layer and a layer below (hereinafter called "nerve fiber layer boundary), $L_3$ denotes a visual cell internal junction, and $L_4$ denotes a retinal pigment epithelial boundary.

The state of the retinal layer is significantly meaningful in the imaging diagnosis using OCT. For example, in glaucoma, the nerve fiber layer between the inner limiting membrane $L_1$ and the nerve fiber layer boundary $L_2$ becomes thinner as the disease progresses. In age-related macular degeneration, a choroidal neovascular is generated at the lower part of the retinal pigment epithelial boundary $L_4$. Therefore, the retinal pigment epithelial boundary $L_4$ is deformed.

The retinal layer boundary needs to be detected first for quantitative and objective measurement of the change in the state of the retinal layer. Therefore, a technique for using an image analysis technique to detect the boundaries of the retinal layers is being developed. A technique for identifying the retinal layer boundary described in U.S. Pat. No. 6,293,674 focuses on a point that the luminance variations from the parts other than the retinal layer are large at the inner limiting membrane and the retinal pigment epithelial boundary. Two strong edges are detected in each A scan line. The edge with smaller Z coordinate values is set as the inner limiting membrane, and the edge with larger Z coordinate values is set as the retinal pigment epithelial boundary.

However, strong edges are just detected and associated in each A scan line in the retinal layer boundary detection described in U.S. Pat. No. 6,293,674. Therefore, if the retinal layer boundary is imaged so that part of the boundary extends above the two-dimensional tomographic image as shown in FIGS. 4A and 4B, there is a problem that the detection of the retinal layer boundary fails because two strong edges are associated with different boundaries. A false detection of the retinal layer boundary can be prevented if the A scan lines without the retinal layer boundary are detected in advance, and the retinal layer boundary is detected only by the A scan lines with the retinal layer boundary. However, it is difficult to identify the A scan lines without the retinal layer boundary without detecting the retinal layer boundary.

SUMMARY OF THE INVENTION

The present invention has been made to solve the problem, and the present invention effectively prevents false detection of the retinal layer boundary. The present invention particularly prevents false detection of the retinal layer boundary even if the retinal layer boundary extends above or below the image.

According to one aspect of the present invention, an image processing apparatus for supporting imaging diagnosis of an eye is provided. The image processing apparatus includes an acquisition unit configured to acquire a tomographic image of an examined eye, a detection unit configured to detect a layer boundary of a retina region from the acquired tomographic image, a determination unit configured to determine a position where the detected layer boundary intersects with an upper limit position or a lower limit position of the image in a depth direction of layers as a dividing position of the tomographic image, a dividing unit configured to divide the tomographic image at the dividing position determined by the determination unit based on scan lines in the depth direction of the layers, and a judgment unit configured to judge, for each region divided by the dividing unit, whether the detection by the detection unit is a false detection, wherein the judgment unit calculates, for each of the divided regions, an average density value of the image outside the retina region according to a detection result of the detection unit and judges that the detection in the divided region by the detection unit is a false detection if the average density value is equal to or greater than a predetermined threshold.

Further features of the present invention will become apparent from the following description of exemplary embodiments (with reference to the attached drawings).

DESCRIPTION OF THE EMBODIMENTS

First Embodiment

Hereinafter, a first embodiment of the present invention will be described with reference to the drawings. An image processing apparatus according to the present embodiment divides a tentatively detected retinal layer boundary into a plurality of retinal layer boundaries and performs judgment in each retinal layer boundary to identify a false detection in A scan lines in which the retinal layer boundary is cut out at the top of the image. In the present embodiment, a position where the tentatively detected retinal layer boundary touches the top of the image (where distance between the tentatively detected retinal layer boundary and the top of the image becomes less than or equal to a certain value) is identified, and the retinal layer boundary is divided based on the position. Whether the divided retinal layer boundaries are real is judged to identify the false detection.

Figure 1:
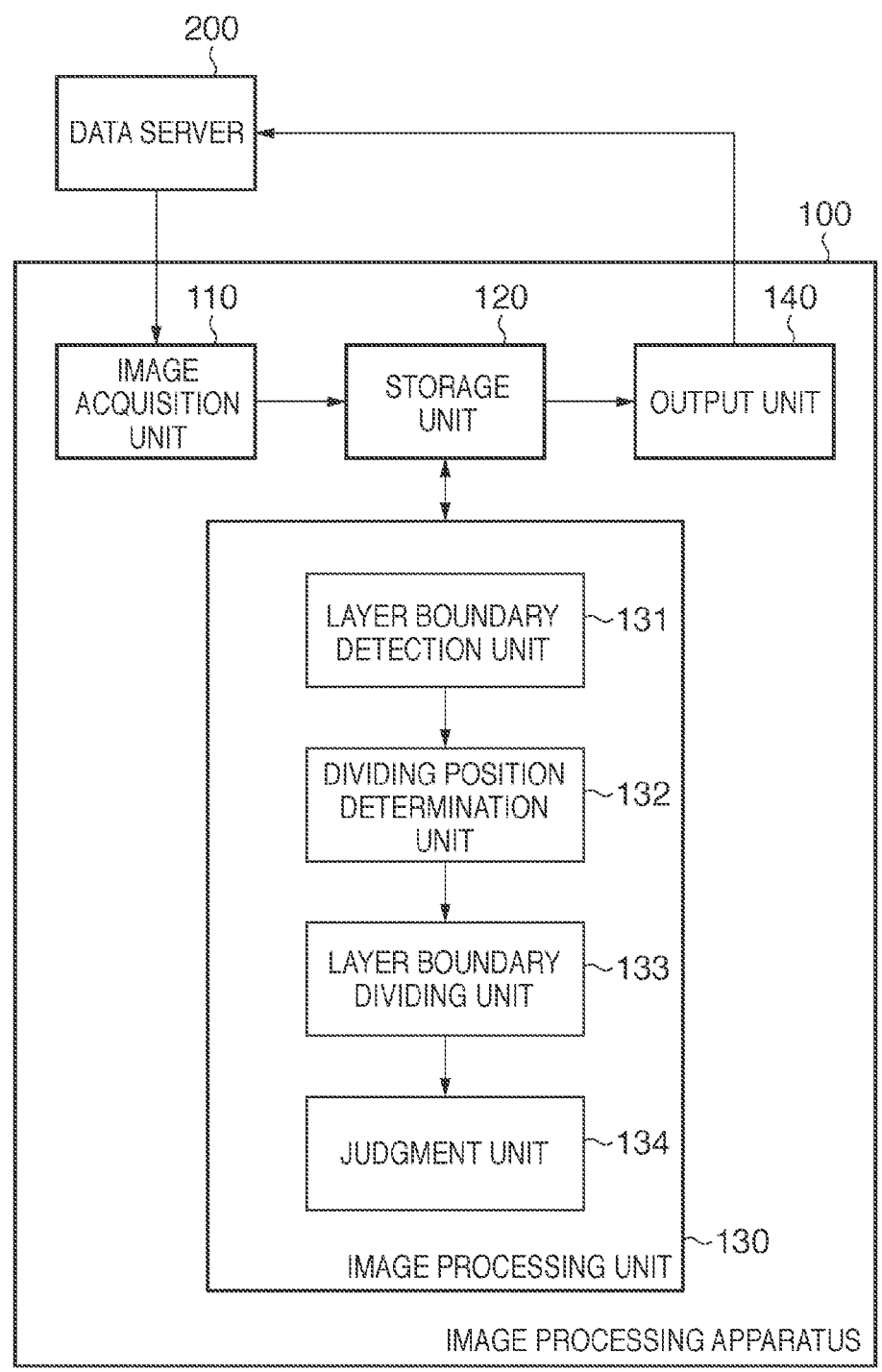
FIG. 1 is a diagram showing a functional configuration of an image processing apparatus according to embodiments.

FIG. 1 shows a configuration of an image processing apparatus 100 that supports imaging diagnosis of eyes in the present embodiment. The image processing apparatus 100 includes an image acquisition unit 110, a storage unit 120, an image processing unit 130, and an output unit 140. The image processing unit 130 includes a layer boundary detection unit 131, a dividing position determination unit 132, a layer boundary dividing unit 133, and a judgment unit 134. The image processing apparatus 100 is connected to an external data server 200 that stores OCT images.

Figure 2:
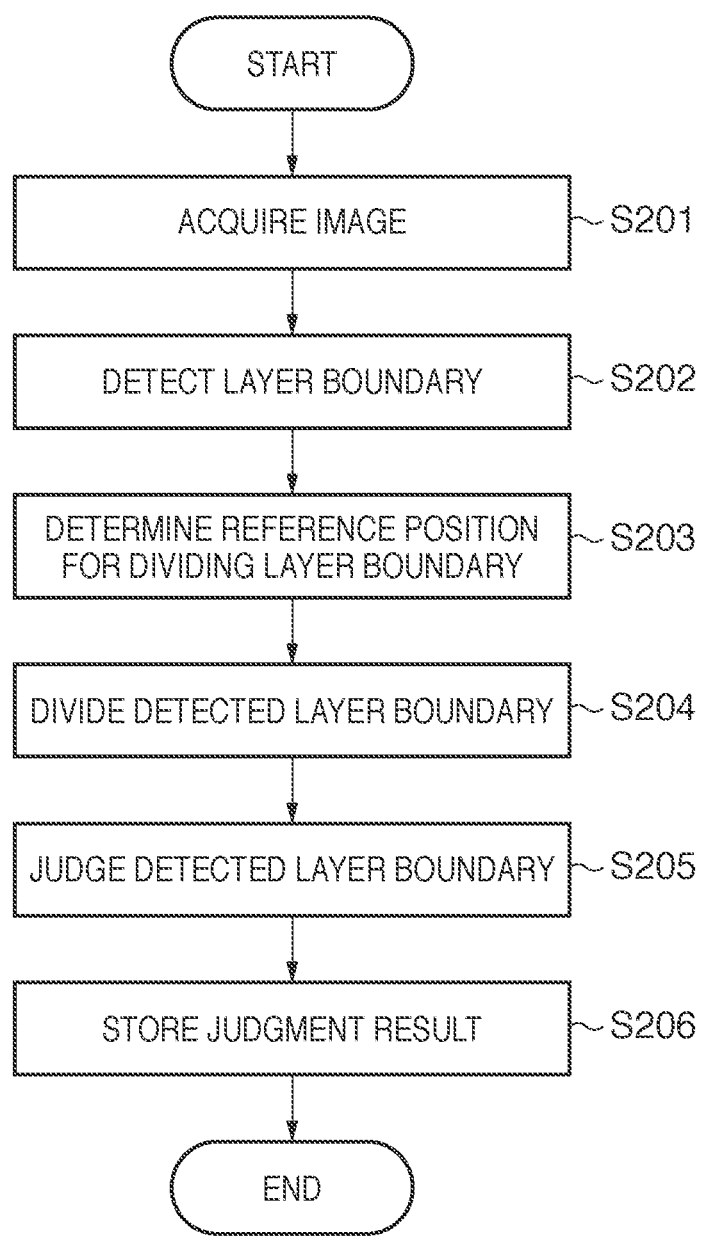
FIG. 2 is a flow chart showing a processing procedure of the image processing apparatus according to the embodiments.

A processing procedure of the image processing apparatus 100 of the present embodiment will be illustrated with reference to FIG. 2. In the present embodiment, an example of judgment of false detection of an inner limiting membrane as a top layer of the retina region will be illustrated to describe the processing procedure of the image processing apparatus 100. However, the present invention is not limited to the false detection judgment of the inner limiting membrane. The present invention can also be applied to false detection judgment of other retinal layer boundaries, such as a nerve fiber layer boundary, a visual cell internal junction, and a retinal pigment epithelial boundary.

The image acquisition unit 110 acquires OCT images, which are tomographic images of an examined eye stored in the data server 200, and stores the OCT images in the storage unit 120 (S201). The layer boundary detection unit 131 tentatively detects a boundary of a retinal layer, such as an inner limiting membrane, from each tomographic image $T_k$ of the OCT images stored in the storage unit 120 (S202). The tentative detection of the inner limiting membrane denotes acquisition of coordinate values in the Z-axis direction of the inner limiting membrane for each A scan line of the tomographic image $T_k$.

The following is a specific process. A smoothing filter is first applied to the target tomographic image $T_k$ to remove noise components. An edge detection filter is applied to the image after the noise smoothing to generate an edge enhanced image. Each A scan line of the image after the edge enhancement is scanned in the positive direction of the Z-axis direction, and the first pixel with a value higher than a certain threshold is set as the inner limiting membrane.

Figure 4A:
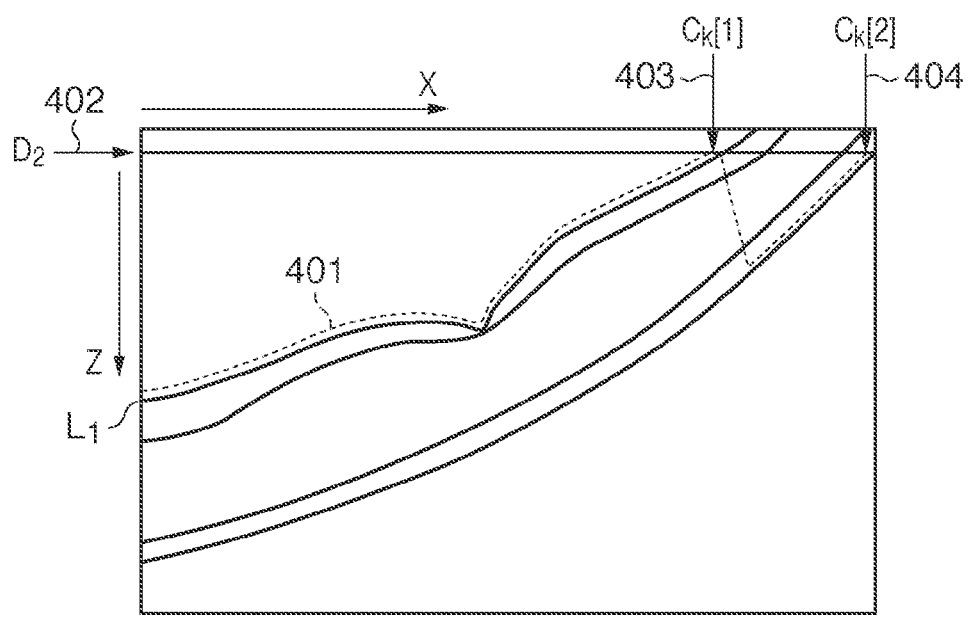
FIGS. 4A and 4B are diagrams explaining a process of identifying a false detection section of an inner limiting membrane according to the embodiments.
Figure 4B:
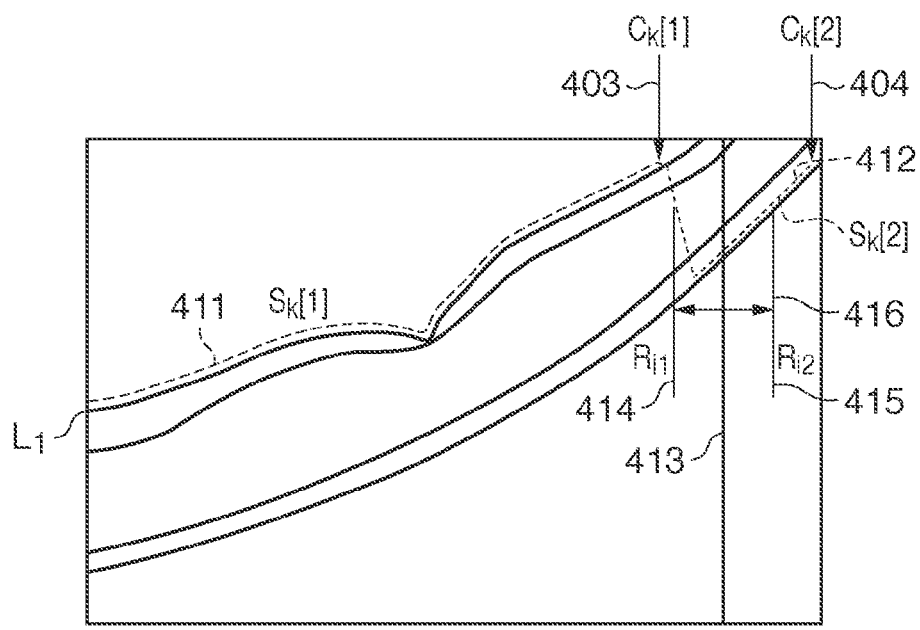

FIGS. 4A and 4B show examples of tomographic images in which the inner limiting membrane is cut out at the top of the image. In FIGS. 4A and 4B, the X axis denotes the horizontal direction of the layers, and the Z axis denotes the depth direction of the layers. The lines parallel to the Z axis of the tomographic image denotes A scan lines. In FIG. 4A, a dotted line 401 denotes a tentative detection result of the inner limiting membrane $L_1$.

The position of the inner limiting membrane tentatively detected in step S202 will be described as $S_k=\{P_{k1}, P_{k2}, \ldots, P_{kl}\}$. In this case, $P_{ki}$ denotes the Z coordinate value of the inner limiting membrane at an i-th A scan line of the tomographic image $T_k$, and $S_k$ denotes a set of Z coordinate values of the inner limiting membrane identified in the tomographic image $T_k$.

The dividing position determination unit 132 determines a position for dividing the inner limiting membrane based on the position information $S_k=\{P_{k1}, P_{k2}, \ldots, P_{kl}\}$ of the inner limiting membrane tentatively detected in step S202 (S203). For example, a position where the inner limiting membrane detected in S202 intersects with a predetermined upper limit position or lower limit position in the depth direction (Z direction) of the layers is determined as the dividing position. FIG. 4A shows a position (arrow 402) at a predetermined distance $D_z$ from the top of the image as an example of the predetermined upper limit position. The tomographic image is divided by an A scan line which is a line along the depth direction of the layers at a position where the line of $D_z$ indicating the predetermined upper limit position and the inner limiting membrane intersect, that is an A scan line where $P_{ki}=D_z$. In the example of FIG. 4A, it can be understood that the dotted line 401 indicating the tentative detection result of the inner limiting membrane passes within the distance $D_z$ from the top of the image at the position of an arrow 403 and the position of an arrow 404. Although not illustrated in FIGS. 4A and 4B, the same process can also be executed for the lower limit position.

Figure 3:
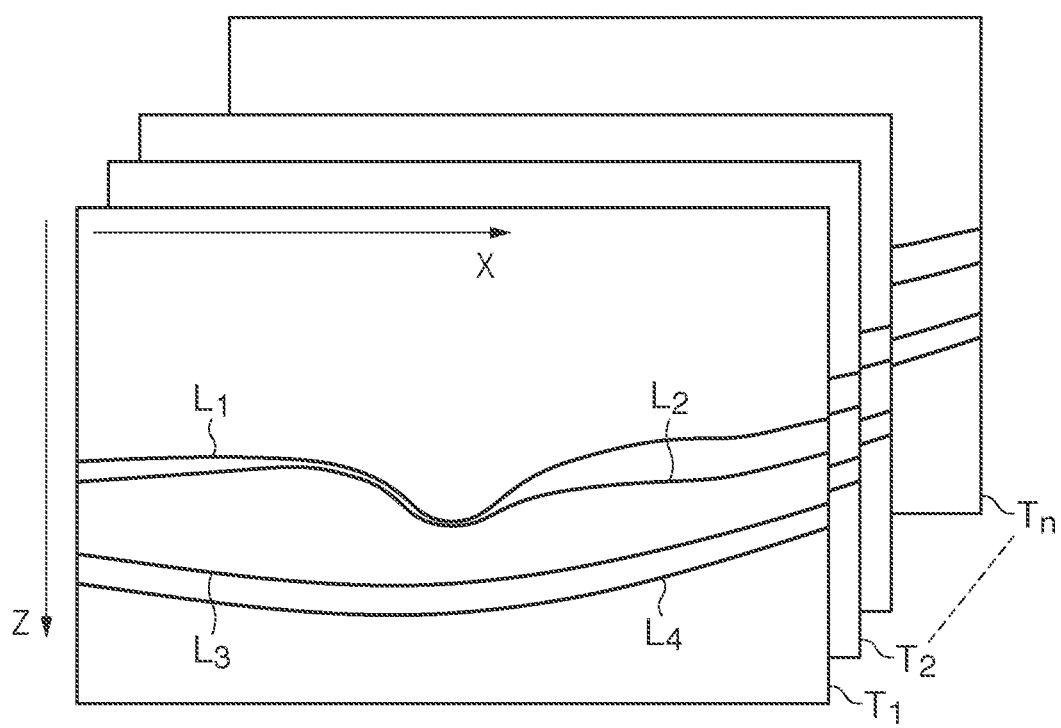
FIG. 3 is a diagram showing an example of a volume image acquired by OCT.

The determination method of the dividing position of the inner limiting membrane is not limited to the method. For example, the dividing position can be determined from a retina region acquired from the tomographic image (region within $L_1$ to $L_4$ of the tomographic image shown in FIG. 3). Specifically, the retina region in the tomographic image is acquired, and a region within a certain distance from the top of the image in the acquired retina region is identified. Positions of both ends of the identified region are set as the dividing positions of the inner limiting membrane. The retina region can be identified by simple binarization processing for the tomographic image. An empirically determined fixed value may be used for a threshold in the binarization processing, or discriminant analysis or P-tile method may be used to determine the threshold in accordance with the inputted OCT image.

Hereinafter, the dividing positions identified in the present step will be described as $C_k=\{C_k[1], C_k[2], \ldots, C_k[m]\}$. In this case, $C_k[i]$ denotes an X coordinate value of an i-th dividing position in the tomographic image $T_k$. The second suffix i of $C_k[i]$ is an index attached to the identified dividing position. More specifically, a case of $C_k=\{C_k[1], C_k[2], \ldots, C_k[m]\}$ denotes that m dividing positions are identified in the tomographic image $T_k$. In the tomographic image shown in FIG. 4A, the positions indicated by the arrows 403 and 404 are the identified dividing positions. Therefore, the dividing positions in the tomographic image are described as $C=\{C_k[1], C_k[2]\}$.

The layer boundary dividing unit 133 divides the tomographic image at the dividing positions determined in step S203 based on the A scan lines along the depth direction of the layers (S204). A set $S_k$ of Z coordinate values of the inner limiting membrane detected in step S202 is divided into a plurality of subsets. For example, it is assumed that the inner limiting membrane detected in step S202 is $S_k=\{P_{k1}, P_{k2}, \ldots, P_{kl}\}$, and the dividing positions of the tomographic image $T_k$ determined in step S203 are $C_k=\{C_k[1], C_k[2], \ldots, C_k[m]\}$. In the present step, subsets $S_k[1], S_k[2], \ldots, S_k[m+1]$ are generated, in which $S_k[1]=\{P_{k1}, \ldots, P_{k,Ck[1]}\}$, $S_k[2]=\{(P_{k,Ck[1]+1}, \ldots, P_{k,Ck[2]}\}, \ldots, S_k[m+1]=\{P_{k,Ck[m]+1}, \ldots, P_{kl}\}$. In the tomographic image shown in FIG. 4B, two sections indicated by the arrows 403 and 404 are the dividing positions determined in the previous step S203. In the dividing process of the present step, the tentative detection result of the inner limiting membrane indicated by the dotted line 401 is divided into the subset $S_k[1]$ indicated by a broken line 411 and the subset $S_k[2]$ indicated by a dotted line 412 based on the dividing positions.

For each divided region, the judgment unit 134 judges whether the tentative detection of the inner limiting membrane in S202 is a false detection (S205). The judgment is performed in each A scan line of the tomographic image. In general, the accuracy of the judgment improves if the detection result obtained in an A scan line near the target A scan line is used in making the judgment in addition to the detection result obtained in the target A scan line. Therefore, the neighborhood detection result is also used in the present step.

In the present invention, the subsets generated in step S204 are used to determine the neighborhood A scan line. Setting of the neighborhood in the i-th A scan line of the tomographic image $T_k$ will be described with reference to FIG. 4B. In FIG. 4B, an A scan line 413 is set as the i-th A scan line of the tomographic image $T_k$. The A scan line 413 is an A scan line between the dividing positions $C_k[1]$ and $C_k[2]$. In this case, a neighborhood $N_i$ of the A scan line 413 is set as $[R_{i1}, R_{i2}]$. Here, $R_{i1}$ and $R_{i2}$ can be obtained by the following Expressions (1) and (2).

$$R_{i1} = \begin{cases} i - R_0 & (\text{if } i - R_0 > C_k[1] + 1) \\ C_k[1] + 1 & (\text{otherwise}) \end{cases} \quad (1)$$

$$R_{i2} = \begin{cases} i + R_0 & (\text{if } i + R_0 < C_k[2]) \\ C_k[2] & (\text{otherwise}) \end{cases} \quad (2)$$

In Expressions (1) and (2), $R_0$ denotes a constant indicating the size of the neighborhood and is empirically determined. In FIG. 4B, the position indicated by a straight line 414 is $R_{i1}$, and the position indicated by a straight line 415 is $R_{i2}$. A section 416 between the two straight lines is the neighborhood $N_i$ related to the i-th A scan line.

After the calculation of the neighborhood $N_i$ for the i-th A scan line, false detection is judged based on density values of the image. In general, the density values of the retina region (region within $L_1$ to $L_4$ in FIG. 3) are higher than the density values outside the retina region (region above $L_1$ of FIG. 3 and region below $L_4$). Therefore, an average $I_{k,i}$ of the density values of a region outside the retina region (for example, above the detected inner limiting membrane) according to the detection result is calculated by the following expression. The value is compared with $T_{intensity}$. If the value is equal to or greater than a threshold, it is determined that $S_k[i]$ is a result of false detection of the inner limiting membrane in the A scan line without the inner limiting membrane, and "false" is stored in a flag $F_k[i]$ indicating the judgment result. On the other hand, if the average density value outside the retina region is smaller than the threshold $T_{intensity}$, it is assumed that the inner limiting membrane is correctly detected, and "true" is stored in the flag $F_k[i]$.

$$I_{k,i} = \sum_{x \in N_i} \sum_{z=P_{kx}-Z_i}^{P_{kx}} I_k(x, z)/N_i \quad (3)$$

In this case, $I_k(x,y)$ denotes density values in coordinates (x,z) of the tomographic image $T_k$. Furthermore, $Z_i$ denotes a parameter for determining in which range above the inner limiting membrane (negative direction of the Z axis in the tomographic image) the average density value will be calculated. Lastly, $N_i$ denotes the number of pixels used to calculate the average density value.

Lastly, the flag $F_k[i]$ indicating the judgment result is stored in the storage unit 120 (S206). Subsequently, the output unit 140 transmits the flag $F_k[i]$ stored in the storage unit 120 to the data server 200.

Although an example of the inner limiting membrane has been illustrated to describe the false detection judgment in the present embodiment, the present invention can also be applied to the false detection judgment of the visual cell internal junction $L_3$ and the retinal pigment epithelial boundary $L_4$. As for the false detection judgment of the visual cell internal junction $L_3$, the density values of the upper part (between $L_2$ and $L_3$) of the visual cell internal junction are lower than the density values of the lower part (between $L_3$ and $L_4$), just like the inner limiting membrane $L_1$. Therefore, the false detection judgment described in step S205 can be used to judge the false detection of the visual cell internal junction.

Meanwhile, in the retinal pigment epithelial boundary $L_4$, there is a tendency that the density values of the upper part (between $L_3$ and $L_4$) of the retinal pigment epithelial boundary are higher than the density values of the lower part. Therefore, the judgment conditions in step S205 needs to be reversed. Specifically, after the calculation of Expression (3), $F_k[i]$ can be set to "true" if $I_{k,i}$ is equal to or greater than $T_{intensity}$, and conversely, "false" can be stored in $F_k[i]$ if $I_{k,i}$ is smaller than the threshold $T_{intensity}$. Instead of the calculation of Expression (3), the following expression may be used to calculate the average density value of the lower part of the retinal pigment epithelial boundary.

$$I_{k,i} = \sum_{x \in N_i} \sum_{z=P_{kx}+Z'_i}^{P_{kx}+Z''_i} I_k(x, z)/N_i \quad (4)$$

At the lower part of the retinal pigment epithelial boundary, there is a region with high density values called choroidea. To reduce the influence of the choroidea, an average of the density values is calculated at a region $[P_{kx}+Z'_i, P_{kx}+Z''_i]$ (where $Z'_i < Z''_i$) further below the choroidea in Expression (4). After the calculation of the average of the density values in Expression (4), $F_k[i]$ is set to "false" if $I_{k,i}$ is equal to or greater than $T_{intensity}$, and conversely, $F_k[i]$ is set to "true" if $I_{k,i}$ is smaller than the threshold $T_{intensity}$.

According to the configuration, a false detection section of a retinal layer boundary can be identified in the tomographic image in which the retinal layer boundary is cut out at the top and bottom ends of the image.

Second Embodiment

In the first embodiment, an average of density values above the tentatively detected inner limiting membrane is calculated, and the average is compared with a set threshold to judge false detection in relation to a case in which the inner limiting membrane is cut out at the top. The following second embodiment illustrates a judgment method when it is difficult to judge the false detection only with the density values due to the existence of a lesion, etc.

A false detection process in the present embodiment will be described using tomographic images shown in FIGS. 5A and 5B. The existence of a cyst 511 is a big feature in the tomographic image shown in FIG. 5A. The density values of the cyst 511 are similar to the density values at the upper part of the inner limiting membrane $L_1$. Therefore, when the inner limiting membrane is tentatively detected, the detection of the inner limiting membrane fails at the section where the cyst exists (section of a dotted line 515 of FIG. 5A).

In the present embodiment, false detection is judged for each divided layer boundary. In addition to the judgment based on the density values, position information of both ends of the detected layer boundary is used for the judgment. As a result, a false detection section of cyst, which is difficult to identify in the first embodiment, can be correctly judged.

Figure 6:
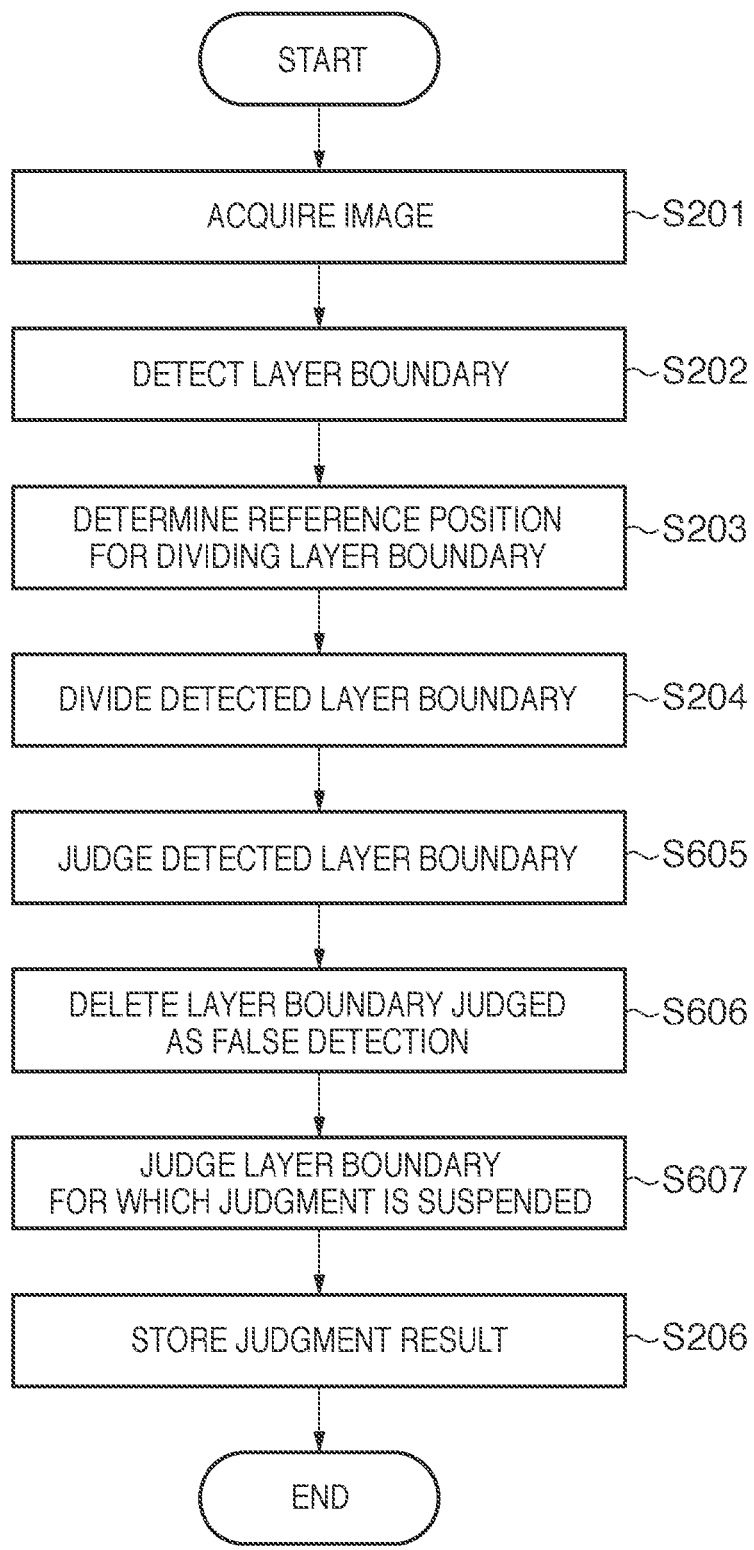
FIG. 6 is a flow chart showing a processing procedure of the image processing apparatus according to the embodiments.

The configuration of the image processing apparatus in the present embodiment can be the same as the configuration of the image processing apparatus 100 in the first embodiment. Hereinafter, a processing procedure of the image processing apparatus 100 of the present embodiment will be illustrated with reference to FIG. 6. The flow chart of FIG. 6 corresponds to the flow chart of FIG. 2 according to the first embodiment. The same processing steps as in FIG. 2 are designated with the same reference numerals, and the description will not be repeated. In place of step S205 of FIG. 2, steps S605, S606, and S607 described below are executed in the present embodiment.

In step S605, the judgment unit 134 performs judgment based on the density values. The judgment is the same as the judgment described in step S205 of the first embodiment. The average density value defined by Expression (3) is calculated in each A scan line, and "false" is stored in the corresponding flag $F_k[i]$ if the average density value is equal to or greater than the threshold $T_{intensity}$. The judgment in the present step is suspended if the average density value is smaller than the threshold. The suspended judgment of the layer boundary is performed in step S607.

Figure 5A:
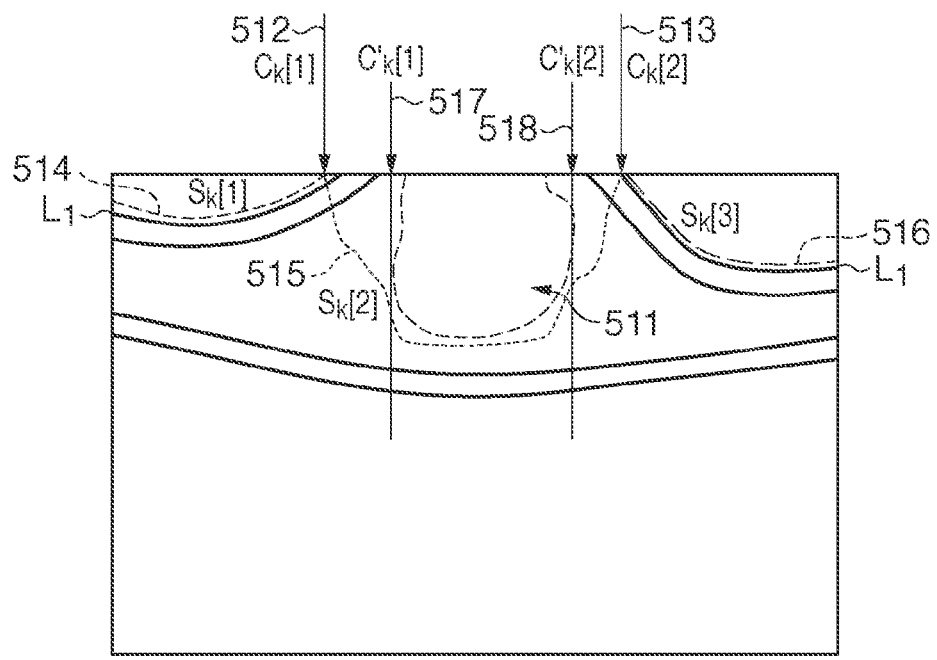
FIGS. 5A and 5B are diagrams explaining a process of identifying a false detection section of the inner limiting membrane according to the embodiments.
Figure 5B:
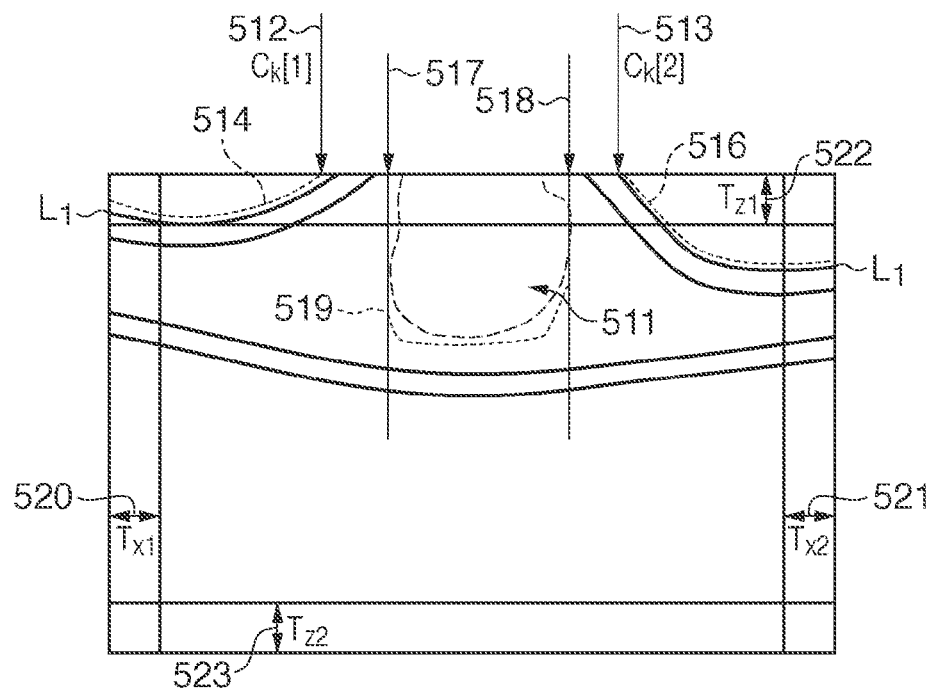

The tentative detection result shown in FIG. 5A is processed as follows in a judgment process of the present step. The judgment of the tentative detection results included in a subset $S_k[1]$ indicated by a dotted line 514 and a subset $S_k[3]$ indicated by a dotted line 516 is suspended. The judgment of the tentative detection result in a range from a straight line 517 to a straight line 518 of a subset $S_k[2]$ indicated by a dotted line 515 is suspended, because the density values of the cyst are similar to the density values of the upper part of the inner limiting membrane $L_1$. On the other hand, flags "false" are provided to the tentative detection results in a range from a dividing position 512 to a straight line 517 and a range from a straight line 518 to a dividing position 513.

In step S606, the judgment unit 134 deletes all tentative detection results provided with the flags "false" from the subset storing the tentative detection results. The tentative detection results in the range from the dividing position 512 to the straight line 517 and the range from the straight line 518 to the dividing position 513 among the tentative detection results shown in FIG. 5A are deleted from the subset $S_k[2]$. Therefore, the elements of $S_k[2]$ are from $S_k[2]=\{P_{k,Ck[1]+1}, \ldots, P_{k,Ck[2]}\}$ to $Sk[2]=\{P_{k,C'k[1]+1}, \ldots, P_{k,C'k[2]}\}$.

In step S607, the judgment unit 134 judges the detection results of the layer boundary for which the judgment is suspended in step S605. In the present step, the judgment is based on the position information of both ends indicating the positions of both ends of the detected layer boundary. As can be seen from the tentative detection results indicated by the dotted lines 514 and 516 of FIG. 5B, the end points of the tentative detection results obtained through step S606 touch at least one of four sides of the image if the inner limiting membrane $L_1$ is properly detected. On the other hand, at a section where the cyst is falsely detected as the inner limiting membrane $L_1$, both ends of the tentative detection results are cut out without touching any vertical and horizontal ends of the image. The present judgment focuses on this point, and if both ends of $S_k[a]$ are away from four sides of the tomographic image by a certain distance or more, it is determined that $S_k[a]$ denotes a result of a false detection of the inner limiting membrane in an A scan line without the inner limiting membrane.

Specifically, the detection is judged as a false detection if the coordinate values of both ends of $S_k[a]$ satisfy the conditional expressions indicated by Expressions (5) and (6). Then, "false" is stored in the flags $F_k[i]$ corresponding to all A scan lines included in $S_k[a]$. On the other hand, "true" is stored in the flags $F_k[i]$ if the conditional expressions are not satisfied. In Expressions (5) and (6), $X_L$ and $X_R$ denote the coordinate values of both ends of each subset $S_k[a]$. As indicated by arrows 520, 521, 522, and 523 of FIG. 5B, $T_{x1}$, $T_{x2}$, $T_{z1}$, and $T_{z2}$ are constants indicating distances from four sides of the tomographic image. Furthermore, $M_x$ denotes the number of pixels in the X-axis direction (the number of A scan lines) of the tomographic image $T_k$, and $M_z$ denotes the number of pixels in the depth direction.

$$T_{x1} < X_L < M_x - T_{x2} \text{ and } T_{z1} < P_{k,X_L} < M_z - T_{z2} \tag{5}$$

$$T_{x1} < X_R < M_x - T_{x2} \text{ and } T_{z1} < P_{k,X_R} < M_z - T_{z2} \tag{6}$$

The detection may be judged as a false detection if one of the conditional expressions (5) and (6) is satisfied, or the detection may be judged as a false detection if the conditional expressions (5) and (6) are satisfied at the same time.

The coordinate values $(1, P_{k1})$ and $(C_k[1], P_{k,ck[1]})$ at both ends of the tentative detection result $S_k[1]$ indicated by the dotted line 514 and the coordinate values $(C_k[2]+1, P_{k,ck[2]+1})$ and $(1, P_{k1})$ at both ends of the tentative detection result $S_k[3]$ indicated by the dotted line 516 do not satisfy the conditional expressions (5) and (6). Therefore, it can be determined that the retinal layer boundary is correctly detected in the section. On the other hand, the coordinate values $(C'_k[1]+1, P_{k,C'k[1]+1})$ and $(C'_k[2], P_{k,C'k[2]})$ of both ends of the tentative detection result $S_k[2]$ indicated by a dotted line 519 satisfy the conditional expressions (5) and (6). Therefore, it can be judged that the section is a false detection section.

The judgment conditions usable in the present step are not limited to the conditions based on the position on the image of the inner limiting membrane. For example, the conditions may be based on the positions on the image of the retinal layer boundary $S_k[a]$. Specifically, the detection may be judged as a false detection if both ends of the subset $S_k[a]$ of the retinal layer boundary are within certain distances from left and right sides of the tomographic image, and the detection may be judged as a correct detection in other cases.

According to the configuration, a false detection section of the retinal layer boundary can be identified in a tomographic image in which the retinal layer boundary is cut out at the top or bottom of the image. Particularly, a false detection can be identified in a tomographic image with cyst as illustrated in FIG. 5B.

The functions of the image processing apparatus 100 in the embodiments can be realized by software on a computer.

Figure 7:
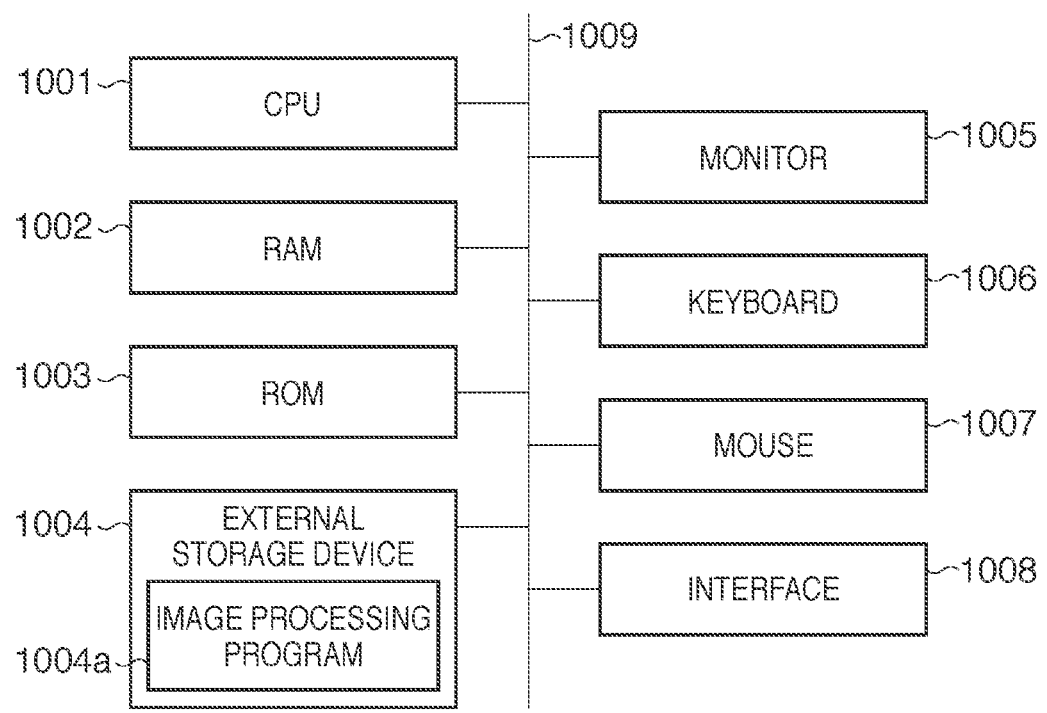
FIG. 7 is a diagram showing an example of configuration of a computer realizing functions of the embodiments.

FIG. 7 is a diagram showing a basic configuration of a computer for realizing the functions of the components of the image processing apparatus 100 by software. A CPU 1001 uses programs and data stored in a RAM 1002 and a ROM 1003 to control the entire computer. The CPU 1001 also controls the execution of software corresponding to the components of the image processing apparatus 100 to realize the functions of the components.

The RAM 1002 includes an area for temporarily storing a program or data loaded from an external storage device 1004 and includes a work area required by the CPU 1001 to execute various processes. The ROM 1003 generally stores a BIOS of the computer, setting data, etc. The external storage device 1004 is a device that functions as a large-capacity information storage device, such as a hard disk drive, and stores an operating system, programs executed by the CPU 1001, etc. An image processing program 1004a for realizing the functions of the image processing unit 130 is stored in, for example, the external storage device 1004. The functions of the storage unit 120 are realized by the RAM 1002 or the external storage device 1004.

A monitor 1005 is constituted by a liquid crystal display, etc., and is capable of displaying a scan image, etc. A keyboard 1006 and a mouse 1007 are input devices, and the operator can use the keyboard 1006 and the mouse 1007 to provide various instructions to the image processing apparatus 100.

An interface 1008 is an interface for communication of various data between the image processing apparatus 100 and an external device (for example, the data server 200). Data acquired through the interface 1008 is imported to the RAM 1002. For example, the functions of the image acquisition unit 110 and the output unit 140 are realized through the interface 1008. The constituent elements are connected to each other by a bus 1009.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-087348, filed Apr. 5, 2010, which is hereby incorporated by reference herein in its entirety.

What is claimed is:

1. An image processing apparatus for supporting imaging diagnosis of an eye, the image processing apparatus comprising:
    an acquisition unit configured to acquire a tomographic image of an examined eye;
    a detection unit configured to detect a layer boundary of a retina region from the acquired tomographic image;
    a determination unit configured to determine a position where the detected layer boundary intersects with an upper limit position or a lower limit position of the image in a depth direction of layers as a dividing position of the tomographic image;
    a dividing unit configured to divide the tomographic image at the dividing position determined by the determination unit based on scan lines in the depth direction of the layers; and
    a judgment unit configured to judge, for each region divided by the dividing unit, whether the detection by the detection unit is a false detection,
    wherein the judgment unit calculates, for each of the divided regions, an average density value of the image outside the retina region according to a detection result of the detection unit and judges that the detection in the divided region by the detection unit is a false detection if the average density value is equal to or greater than a predetermined threshold.

2. The image processing apparatus according to claim 1, wherein
    for the divided region in which the average density value is smaller than the threshold, the judgment unit further
    calculates, for each of the scan lines, an average density value of the image outside the retina region according to the detection result of the detection unit, and
    when the layer boundary at a section where the average density value is equal to or greater than the threshold is deleted, judges that the detection by the detection unit in the divided region is a false detection if there is a section of the layer boundary in which both ends are cut out without touching any vertical and horizontal edges of the image as a result of the deletion.

3. The image processing apparatus according to claim 1, wherein the layer boundary is at least one of a nerve fiber layer boundary, an inner limiting membrane, a visual cell internal junction, and a retinal pigment epithelial boundary.

4. A program for causing a computer to function as said units of the image processing apparatus according to claim 1.

5. An image processing method executed by an image processing apparatus for supporting imaging diagnosis of an eye, the image processing method comprising the steps of:
    acquiring a tomographic image of an examined eye;
    detecting a layer boundary of a retina region from the acquired tomographic image;
    determining a position where the detected layer boundary intersects with an upper limit position or a lower limit position of the image in a depth direction of layers as a dividing position of the tomographic image;
    dividing the tomographic image at the determined dividing position based on scan lines in the depth direction of the layers; and
    judging, for each divided region, whether the detection in the detection step is a false detection,
    wherein in the judgment step, an average density value of the image outside the retina region is calculated for each of the divided regions according to a detection result obtained in the detection step, and the detection in the divided region in the detection step is judged as a false detection if the average density value is equal to or greater than a predetermined threshold.

6. An image processing apparatus for supporting imaging diagnosis of an eye, the image processing apparatus comprising:
    an acquisition unit configured to acquire a tomographic image of an examined eye;
    a detection unit configured to detect a layer boundary of a retina region from the acquired tomographic image; and
    a judgment unit configured to judge that the detection of the layer boundary is a false detection if a density value of a region obtained based on the detected layer boundary is within a predetermined range.

7. The image processing apparatus according to claim 6, further comprising a determination unit configured to determine a position where the detected layer boundary intersects with an upper limit position or a lower limit position of the image in a depth direction of layers as a dividing position of the tomographic image,
wherein the judgment unit judges, for each of regions at the dividing position, whether the detection by the detection unit is a false detection.

8. The image processing apparatus according to claim 7, wherein the judgment unit calculates, for each of the divided regions, an average density value of the image outside the retina region according to a detection result of the detection unit and judges that the detection in the divided region by the detection unit is a false detection if the average density value is equal to or greater than a predetermined threshold.

9. The image processing apparatus according to claim 6, wherein the layer boundary detected by the detection unit is an inner limiting membrane.

10. A program for causing a computer to function as said units of the image processing apparatus according to claim 6.

11. An image processing apparatus for supporting imaging diagnosis of an eye, the image processing apparatus comprising:
an acquisition unit configured to acquire a tomographic image of an examined eye; and
a dividing unit configured to divide the tomographic image based on a position where a layer boundary of a retina region in the acquired tomographic image intersects with an upper limit position or a lower limit position of the image in a depth direction of layers.

12. The image processing apparatus according to claim 11, wherein the dividing unit comprises:
a unit configured to obtain a layer boundary of a retina region from the acquired tomographic image;
a unit configured to determine a position where the obtained layer boundary intersects with an upper limit position or a lower limit position of the image in a depth direction of layers as a dividing position of the tomographic image; and
a unit configured to divide the tomographic image at the dividing position based on scan lines in the depth direction of the layers.

13. The image processing apparatus according to claim 11, further comprising a unit configured to obtain a layer boundary of a retina region from the acquired tomographic image, wherein the obtaining methods differ from region to region of the divided tomographic image.

14. A program for causing a computer to function as said units of the image processing apparatus according to claim 11.

15. An image processing apparatus for supporting imaging diagnosis of an eye, the image processing apparatus comprising:
a unit configured to acquire a tomographic image of an examined eye; and
a unit configured to obtain a layer boundary of a retina region in the acquired tomographic image based on a position where a layer boundary of a retina region in the acquired tomographic image intersects with an upper limit position or a lower limit position of the image in a depth direction of layers, while changing methods for extracting a layer boundary of a retina region.

16. A program for causing a computer to function as said units of the image processing apparatus according to claim 15.

17. An image processing method executed by an image processing apparatus for supporting imaging diagnosis of an eye, the image processing method comprising the steps of:
acquiring a tomographic image of an examined eye;
detecting a layer boundary of a retina region from the acquired tomographic image; and
judging that the detection of the layer boundary is a false detection if a density value of a region obtained based on the detected layer boundary is within a predetermined range.

18. An image processing method executed by an image processing apparatus for supporting imaging diagnosis of an eye, the image processing method comprising the steps of:
acquiring a tomographic image of an examined eye; and
dividing the tomographic image based on a position where a layer boundary of a retina region in the acquired tomographic image intersects with an upper limit position or a lower limit position of the image in a depth direction of layers.

19. An image processing method executed by an image processing apparatus for supporting imaging diagnosis of an eye, the image processing method comprising the steps of:
acquiring a tomographic image of an examined eye; and
obtaining a layer boundary of a retina region in the acquired tomographic image based on a position where a layer boundary of a retina region in the acquired tomographic image intersects with an upper limit position or a lower limit position of the image in a depth direction of layers, while changing methods for extracting a layer boundary of a retina region.

* * * * *